(12) United States Patent
Raskie

(10) Patent No.: US 7,681,444 B2
(45) Date of Patent: Mar. 23, 2010

(54) METHOD AND APPARATUS FOR MEASURING THE DENSITY OF ONE COMPONENT IN A MULTI-COMPONENT FLOW

(75) Inventor: Joey D. Raskie, Katy, TX (US)

(73) Assignee: Micro Motion, Inc., Boulder, CO (US)

(*) Notice: Subject to any disclaimer, the term of this patent is extended or adjusted under 35 U.S.C. 154(b) by 0 days.

(21) Appl. No.: 11/993,716

(22) PCT Filed: Jun. 29, 2005

(86) PCT No.: PCT/US2005/023667

§ 371 (c)(1),
(2), (4) Date: Dec. 21, 2007

(87) PCT Pub. No.: WO2007/005024

PCT Pub. Date: Jan. 11, 2007

(65) Prior Publication Data

US 2008/0307891 A1  Dec. 18, 2008

(51) Int. Cl.
G01F 15/08 (2006.01)
G01N 9/00 (2006.01)
G01N 1/14 (2006.01)

(52) U.S. Cl. .................. 73/200; 73/32 R; 73/861.354; 73/863.83

(58) Field of Classification Search .................. None
See application file for complete search history.

(56) References Cited

U.S. PATENT DOCUMENTS

| | | | | |
|---|---|---|---|---|
| 3,602,033 A | * | 8/1971 | Burrell et al. ................. 73/1.02 |
| 4,773,257 A | * | 9/1988 | Aslesen et al. .............. 73/61.44 |
| 4,776,210 A | * | 10/1988 | Baillie et al. ............. 73/861.04 |
| 4,977,915 A | | 12/1990 | Marrelli |
| 5,259,239 A | * | 11/1993 | Gaisford ..................... 73/61.44 |
| 5,535,632 A | * | 7/1996 | Kolpak .................... 73/861.04 |
| 5,654,502 A | | 8/1997 | Dutton |
| 5,861,561 A | * | 1/1999 | Van Cleve et al. ....... 73/861.52 |
| 6,032,539 A | | 3/2000 | Liu et al. |
| 6,182,505 B1 | * | 2/2001 | Segeral ...................... 73/61.44 |

(Continued)

FOREIGN PATENT DOCUMENTS

KR  2002-67036  8/2002

(Continued)

OTHER PUBLICATIONS

Edelmira Afanador, Oil-Water Separation in Liquid-Liquid Cylindrical Cyclone Separators, A Thesis Submitted in Partial Fulfillment of the Requirements for the Degree of Master of Science in the Discipline of Petroleum Engineering, The Graduate School, The University of Tulsa, 1999, 93 pp.

*Primary Examiner*—Harshad Patel
(74) *Attorney, Agent, or Firm*—The Ollila Law Group LLC

(57) ABSTRACT

A method and apparatus is disclosed that determines the density of one component in a multi-component flow through a conduit. The multi-component flow is separated into two streams (404) where a first stream has essentially all the flow for a first one of the components. The density of the second stream is measured (406).

13 Claims, 4 Drawing Sheets

U.S. PATENT DOCUMENTS

| | | |
|---|---|---|
| 6,758,964 B2 | 7/2004 | Roudile et al. |
| 2003/0136185 A1 | 7/2003 | Dutton et al. |
| 2006/0053869 A1* | 3/2006 | Gysling et al. ............. 73/61.44 |
| 2006/0096388 A1* | 5/2006 | Gysling et al. ........... 73/861.03 |
| 2006/0123923 A1* | 6/2006 | Dutton et al. .......... 73/861.354 |
| 2007/0006640 A1* | 1/2007 | Gysling ..................... 73/61.44 |
| 2007/0006727 A1* | 1/2007 | Gysling ........................... 95/1 |
| 2008/0000306 A1* | 1/2008 | Agar et al. ................ 73/861.04 |
| 2009/0139345 A1* | 6/2009 | Xie ......................... 73/861.04 |

FOREIGN PATENT DOCUMENTS

| | | |
|---|---|---|
| RU | 2002120181 A | 2/2004 |
| WO | WO 01/31298 A2 | 5/2001 |

* cited by examiner

METHOD AND APPARATUS FOR MEASURING THE DENSITY OF ONE COMPONENT IN A MULTI-COMPONENT FLOW

BACKGROUND OF THE INVENTION

1. Field of the Invention

The invention is related to the field of well flow measurements, and in particular, to oil flow computers.

2. Description of the Prior Art

Gas and oil wells may have multi-phase flow exiting from the well head. The total flow from the well head needs to be measured. To measure the total flow, the gas flow is typically separated from the liquid flow and the gas and liquid flows are measured separately. The gas and liquid flows may be measured by two different Coriolis flow meters. The liquid flow typically contains both oil and water. To accurately measure the amount of oil in the liquid flow, the amount of water in the liquid flow must be determined. To determine the amount of water in the flow, the density of the water needs to be determined. Currently the density of water is determined by periodically taking a sample of the water flowing from the well head and determining the density using a hydrometer. This method has a number of problems. One problem is that the density of the water can change over time. If the density of the water changes and the old density measurement is used, the calculation for the amount of oil in the flow becomes inaccurate. The inaccuracy is more of a problem in high water cut flows than in low water cut flows. One way to minimize the inaccuracies is to frequently sample the water density. However, removing the sample from the system and testing the density may be a labor and time consuming task.

Therefore there is a need for a better system and method for determining the amount of oil in the flow.

SUMMARY OF THE INVENTION

A method and apparatus is disclosed that determines the density of one component in a multi-component flow through a conduit. The multi-component flow is separated into two streams where a first stream has essentially all the flow for a first one of the components. The density of the second stream is measured.

Aspects

One aspect of the invention includes a method for determining the density of one of the components in a multi-component flow comprising, directing a flow of a liquid into a conduit where the liquid is comprised of at least a first material and a second material, the steps of the method characterized by:

separating the flow of the liquid into a first stream and a second stream with a rate of flow in the first stream being greater than a rate of flow in the second stream and where the first stream contains essentially all of the first material;

measuring the density of the liquid in the second stream.

Preferably, the method further comprises where the first material being oil.

Preferably, the method further comprises where the second material being water.

Preferably, the method further comprises where the second material being denser than the first material.

Preferably, the method further characterized by:

measuring the temperature of the liquid flowing in the second stream.

Preferably, the method further characterized by:

measuring the total flow of material through the conduit;

determining the amount of the first material flowing in the conduit based in part on the density of the liquid in the second stream.

Preferably, the method further characterized by gravity being used to separate essentially all of the first material into the first stream.

Another aspect of the invention comprises a method for determining the density of one of the components in a multi-component flow comprising, directing a flow of a liquid into a conduit where the liquid is comprised of at least oil and water; where the steps of the method are characterized by:

continuously separating a small sample of water from the liquid flowing in the conduit and measuring the density of the water.

Preferably, the method characterized by having the density of the water measured using a Coriolis flow meter.

Preferably, the method characterized by having the density of the water continuously measured.

Preferably, the method further characterized by:

determining the amount of oil flowing in the conduit based in part on the measured density of the water.

Preferably, the method further characterized by:

using the density of the water to determine the water cut of the liquid.

Another aspect of the invention comprises a device for determining the density of one of the components in a multi-component flow the device having a first conduit configured to contain a liquid comprised of at least a first material and a second material, the device characterized by:

a second conduit coupled to the first conduit and configured to draw a sample of the second material from the liquid;

a first Coriolis flow meter coupled to the second conduit and configured to measure the density of the sample of the second material in the second conduit.

Preferably, the device with the second conduit further characterized by:

a separator tank having a top half and a bottom half, where the first conduit flows into the separator tank and the second conduit is coupled to the bottom half of the separator tank.

Preferably, the device further characterized by:

a second Coriolis flow meter attached to the first conduit and configured to measure the density of the liquid flowing in the first conduit;

a processor connected to the first and second Coriolis flow meters and configured to determine the ratio of the first material with respect to the second material in the liquid in the conduit based, in part, on the density measurement from the first Coriolis flow meter.

Preferably, the device characterized by the first conduit having a first diameter and the second conduit having a second diameter and the first diameter is larger than the second diameter.

Preferably, the device characterized by the second diameter is less than $\frac{1}{10}$ the first diameter.

Preferably, the device characterized by the first conduit having a first flow rate and the second conduit having a second flow rate and the first flow rate is larger than the second flow rate.

Another aspect of the invention comprises a device for determining the density of one of the components in a multi-component flow the device having a conduit containing a flowing liquid comprised of at least a first material and a second material, the device characterized by:

a means for separating the flowing liquid into a first stream and a second stream with a rate of flow in the first stream being greater than a rate of flow in the second stream and where the first stream contains essentially all of the first material, a means for measuring the density of the material in the second stream.

DETAILED DESCRIPTION OF THE PREFERRED EMBODIMENT

Figure 1:
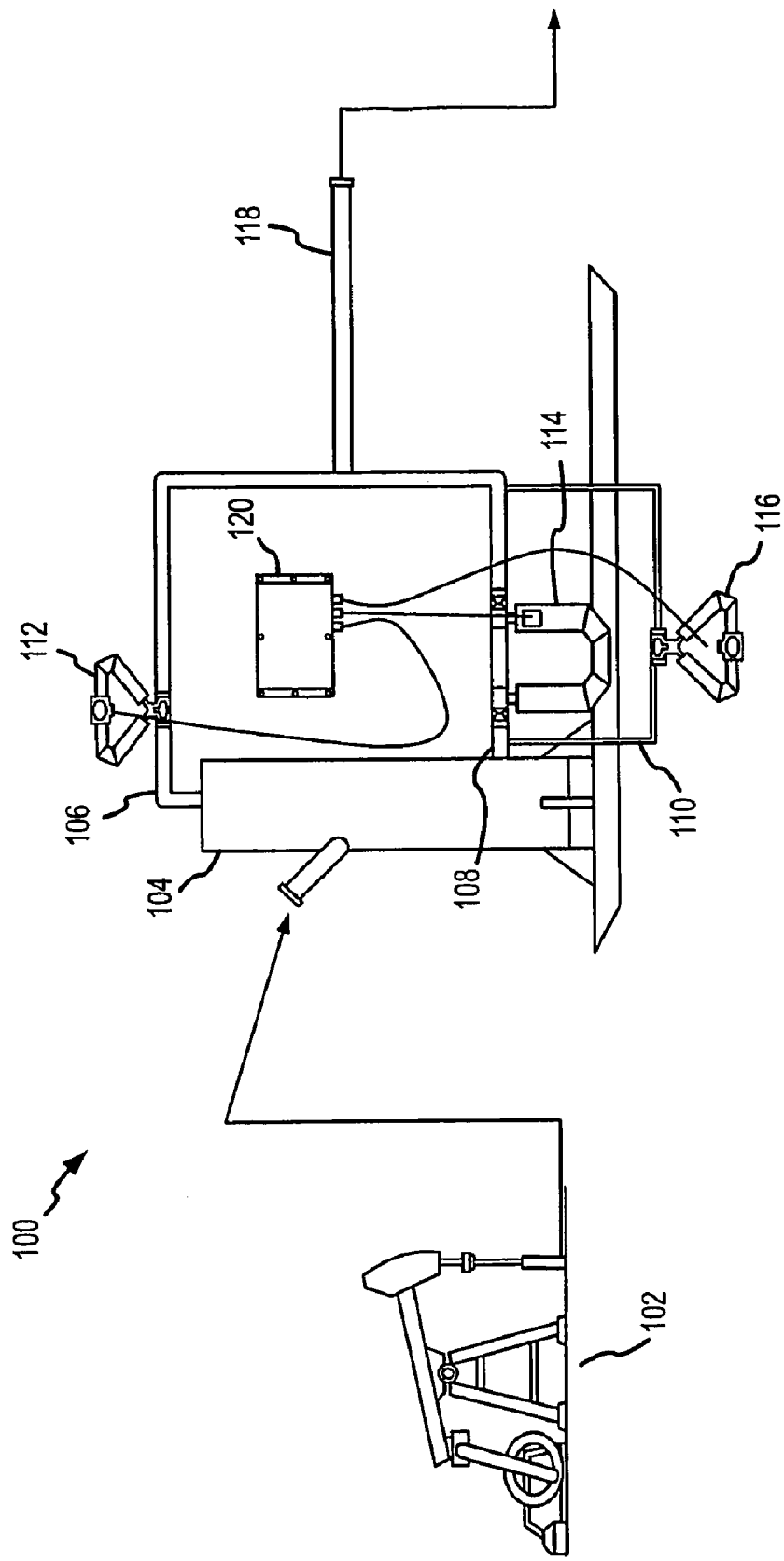
FIG. 1 is a diagram of an oil and gas measurement system 100 in an example embodiment of the invention
Figure 2:
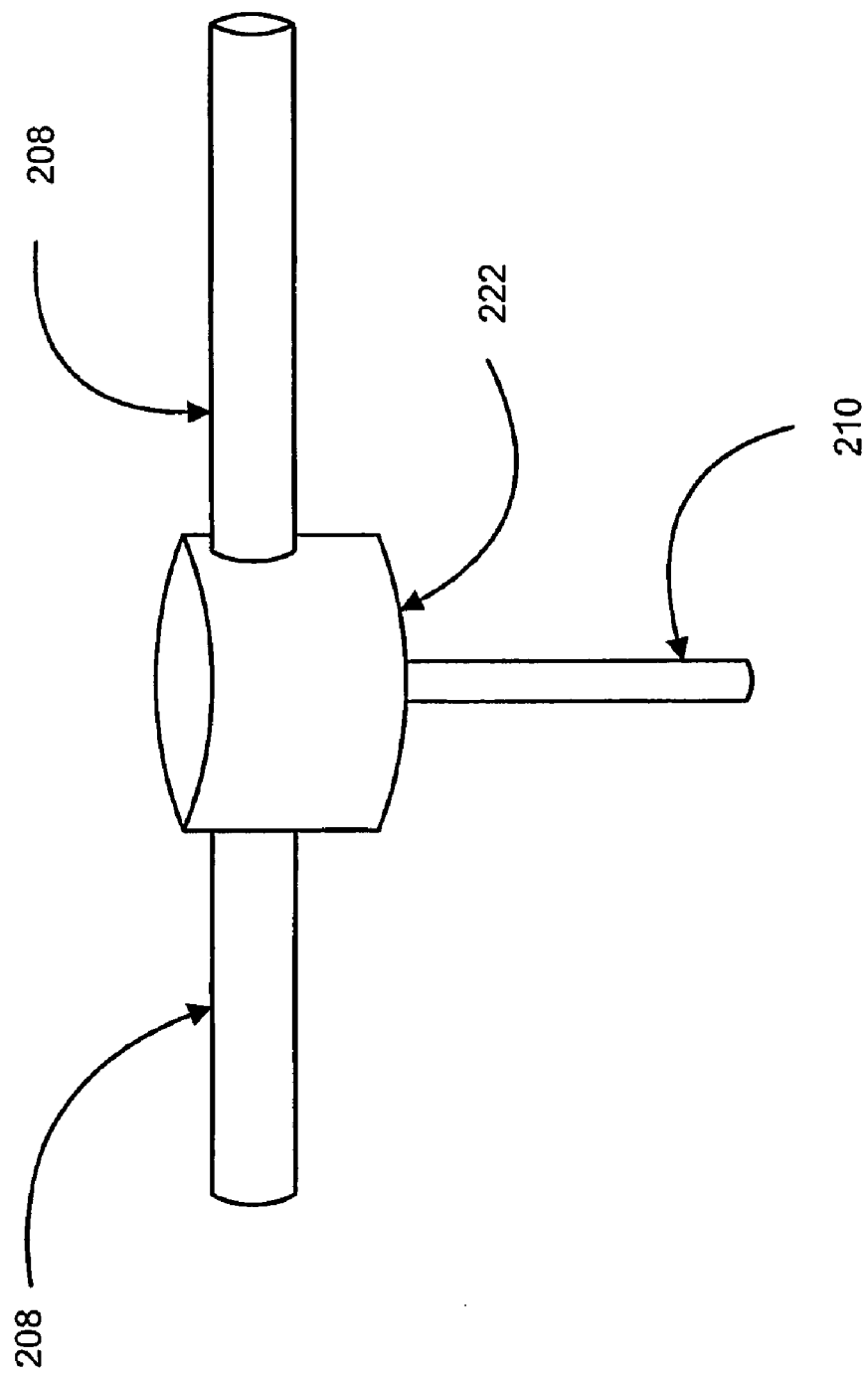
FIG. 2 is a drawing of knock out leg in another example embodiment of the invention.
Figure 3:
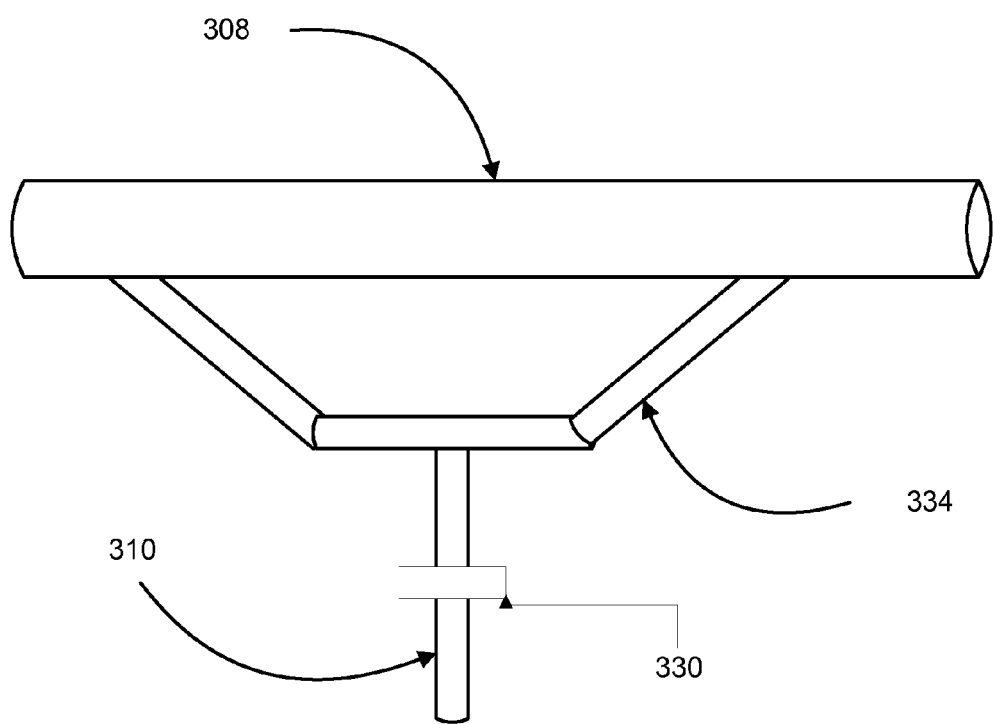
FIG. 3 is a drawing of knock out leg using a separator tank in another example embodiment of the invention.

FIGS. 1-3 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents, FIG. 1 is a diagram of an oil and gas measurement system 100 in an example embodiment of the invention. Oil and gas measurement system 100 is connected to a well head 102 and comprises: Separator 104, liquid outlet pipe 108, gas outlet pipe 106, water knock out leg 110, flow meters 116, 114, and 112, system outlet pipe 118, and oil computer 120.

In operation well head 102 produces a multi-phase flow that may contain gas, oil, water, and debris, for example silt or sand. The multi-phase flow is sent to separator 104 where the gas is separated from the liquid. Separator 104 may be any type of separator including a Gas-Liquid Cylindrical Cyclone (GLCC) separator. Gas outlet pipe 106 removes gas from the top of separator 104. Flow meter 112 measures the amount of gas flowing through gas outlet pipe 106. Flow meter 112 may be any type of flow meter, including a turbine flow meter, a Coriolis flow meter, or the like. Liquid is removed from separator 104 by liquid outlet pipe 108. The liquid flowing in liquid outlet pipe 108 may contain oil and water. Water knock out leg 110 is configured to separate a small stream of water from liquid outlet pipe 108. Flow meter 114 measures the flow of liquid in liquid outlet pipe 108. In one example embodiment of the invention, flow meter 114 is a Coriolis flow meter. When flow meter 114 is a Coriolis flow meter, flow meter 114 can be used to measure the density of the liquid flowing through liquid outlet pipe 108. The water cut value of the liquid flowing in liquid outlet pipe 108 can be determined using the measured density of the liquid and equation 1.

$$WC = \frac{\rho(\text{mix}) - \rho(\text{oil})}{\rho(\text{water}) - \rho(\text{oil})} \quad \text{Equation 1}$$

where $\rho(\text{mix})$ is the density of the liquid, $\rho(\text{oil})$ is the density of the oil in the liquid, and $\rho(\text{water})$ is the density of the water in the liquid. The oil density can be entered by the user or measured separately. Equation 1 is dependent on the density of the water flowing in the liquid. The water density can vary as a function of salinity.

Flow meter 116 measures the flow of water in water knock out leg 110. Flow meter 116 is a Coriolis flow meter. Flow meter 116 also measures the density of water flowing in water knock out leg 110. The flow from water knock out leg 110 may be re-inserted back into liquid outlet pipe 108 after flow meter 114 (as shown) or may be re-inserted before flow meter 114 (not shown). When the flow from water knock out leg 110 re-enters liquid outlet pipe 108 before flow meter 114, then flow meter 116 does not need to be used to measure flow, it's uses can be dedicated for measuring the density of the material flowing in water knock out pipe 110. Oil computer 120 monitors flow meters 112, 114, and 116 to determine the total flow through the system. In one example embodiment the gas and liquid outputs may be recombined into one system outlet pipe 118. In other example embodiments of the invention the gas and liquids may be sent to separate destinations through separate piping systems (not shown).

Oil computer 120 monitors the flow through flow meters 112, 114, and 116. The liquid flowing in liquid outlet pipe 108 comprises a mix of oil and water. To determine the amount of oil flowing through liquid outlet pipe 108, the amount of water must be determined. To determine the amount of water flowing through liquid outlet pipe 108, the density of the water must be determined. Coriolis flow meters may be used to measure the density of the material flowing through the meter as well as the amount of material flowing through the meter. Water knock out leg 110 is configured to separate a stream of fluid essentially free of oil or other hydrocarbons from the main stream of fluids flowing in liquid outlet pipe 108. The stream of fluid flowing in water knock out leg may be comprised of water, sediment, and other water soluble material, for example salt. A change in the salinity of the water can change the density of the water. Coriolis flow meter 116 is used to measure the density of the fluid flowing in water knock out leg 110. The measured density is then fed back into the calculation for the amount of oil flowing in outlet pipe 108 determined by the water cut equation.

Water knock out leg 110 can be configured in a number of ways to enable a stream of fluid essentially free of oil or lighter liquids to be separated from the main fluid flow in outlet pipe 108. In one example embodiment of the invention, outlet pipe 108 would be a horizontal pipe having a sufficient length with respect to the flow rate to allow the hydrocarbons to rise to the top of the outlet pipe. The water knock out leg 110 would be connected to the bottom of outlet pipe 108, drawing only some of the heavier fluid from the outlet pipe. The water knock out leg 110 may be smaller in diameter than outlet pipe 108 such that the flow into water knock out leg is restricted. In one example embodiment of the invention, water knock out leg 110 is 1/10 the diameter of outlet pipe 108. Only a small stream or sample of the heavier fluid flowing in outlet pipe 108 needs to be drawn into water knock out leg 110. In some cases most of the heavier fluid remains flowing in outlet pipe 108.

FIG. 2 is another configuration for knock out leg in another example embodiment of the invention. Knock out leg comprises separator tank 222 and knock out pipe 210. Outlet pipe 208 flows into separator tank 222. Outlet pipe exits from separator tank 222 near the top of separator tank 222. Knock out pipe 210 exits at or near the bottom of separator tank 222. Separator tank has a volume that allows a retention time for the liquid sufficient for the liquid to stratify inside the tank. The knock out pipe 210 may also be smaller in diameter than outlet pipe 208 such that the flow into knock out leg 210 is restricted. Only a small stream or sample of the heavier fluid flowing into separator tank 222 needs to be drawn into knock out leg 210. In many cases most of the heavier fluid exits from separator tank 222 through outlet pipe 208.

FIG. 3 shows another configuration for a knock out leg in an example embodiment of the invention. Knock out leg comprises separator pipe 334 and knock out pipe 310. Outlet pipe 308 has separator pipe 334 extending from the bottom of outlet pipe 308. Separator pipe 334 may be smaller in diameter than outlet pipe 308. Separator pipe 334 runs below outlet pipe 308 for a short distance before rejoining outlet pipe 308. Knock out pipe 310 is joined to separator pipe 334 at the bottom of separator pipe 334. Only a small stream or sample of the heavier fluid flowing in separator pipe 334 needs to be drawn into knock out leg 310. Knock out pipe 310 may be the same size as separator pipe 334, or may be a smaller size than separator pipe 334. Other configurations may be used to separate a small sample from the multi-phase liquid flowing in the outlet pipe to take advantage of this invention.

Because the density of the water flowing in a multi-phase flow can be measured continuously, salinity changes in the water can be compensated for on a real time bases. This should help reduce the uncertainty in water cut measurements. This invention is not limited to measuring the density of water in an oil and water flow. The invention can be used in any mixed flow where the components can be separated during flow. The knock out leg can be designed to separate any heavier liquid from a lighter liquid. In addition, in some embodiments, the invention may include a temperature measuring device, such as temperature sensor 330. The temperature sensor 330 may be provided in order to measure the temperature of the liquid flowing in the knock out leg 310. It should be appreciated that the temperature sensor 330 may be included in any of the previously described embodiments. The temperature sensor 330 may comprise any well known devices such as a RTD. It should be appreciated that those skilled in the art will readily recognize other temperature measuring devices that can easily be used with the present invention.

Figure 4:
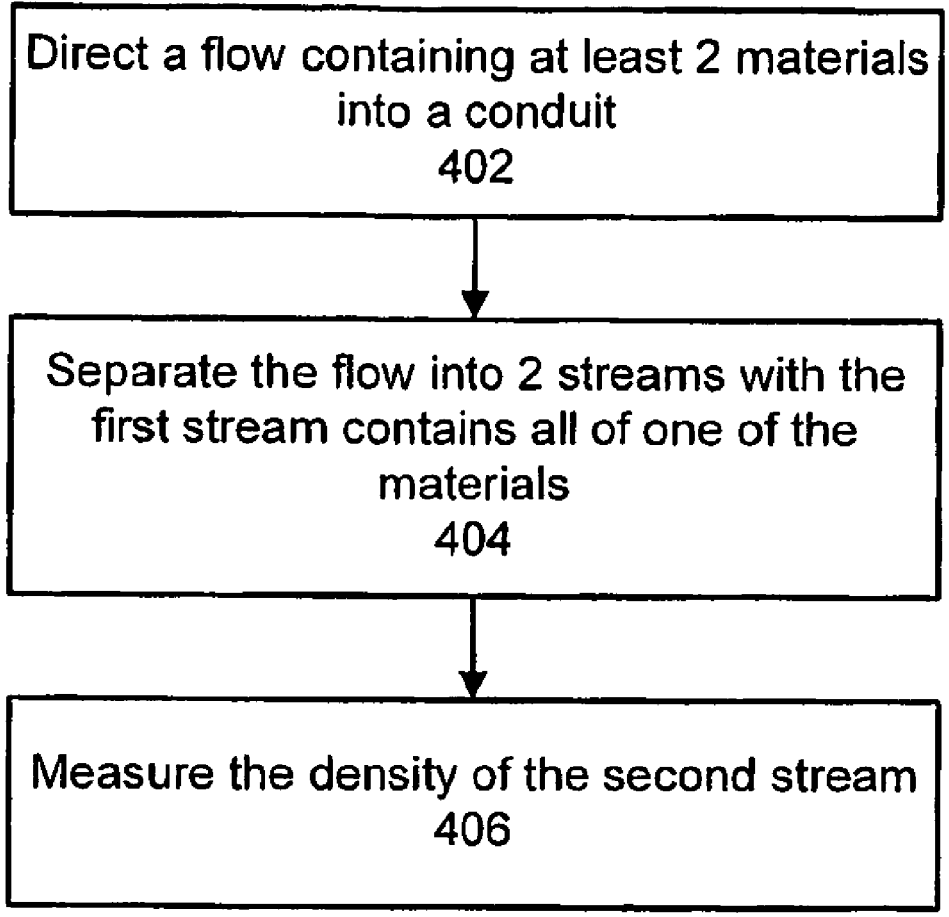
FIG. 4 is a flow chart of a method for determining the density of one of the components in a multi-component flow in one example embodiment of the invention.

FIG. 4 is a flow chart of a method for determining the density of one of the components in a multi-component flow. At step 402 a flow comprising at least a first material and a second material are directed into a conduit. At step 404 the flow of the liquid is separated into a first stream and a second stream where the first stream contains essentially all of the first material. At step 406 the density of the liquid in the second stream is measured.

I claim:

1. A method for determining the density of one of the components in a multi-component flow comprising, directing a flow of a liquid into a conduit where the liquid is comprised of at least a first material and a second material (402), the steps of the method characterized by:

separating the flow of the liquid into a first stream and a second stream where the first stream contains essentially all of the first material (404); and measuring the density of the second material in the second stream (406) while a rate of flow of the first stream is greater than a rate of flow of the second stream.

2. The method of claim 1 characterized by the first material being oil.

3. The method of claim 1 characterized by the second material being water.

4. The method of claim 1 characterized by the second material being denser than the first material.

5. The method of claim 1 further characterized by:
measuring the temperature of the second material flowing in the second stream.

6. The method of claim 1 further characterized by:
measuring the total flow of material through the conduit;
determining the amount of the first material flowing in the conduit based in part on the density of the second material in the second stream.

7. The method of claim 1 characterized by gravity being used to separate essentially all of the first material into the first stream.

8. A device for determining the density of one of the components in a multi-component flow the device having a first conduit (108) configured to contain a flowing liquid comprised of at least a first material and a second material, the device characterized by:

a second conduit (110) coupled to the first conduit (108) and configured to draw a sample of substantially only the second material from the flowing liquid in the first conduit (108);

a first Coriolis flow meter (116) coupled to the second conduit (110) and configured to measure the density of the sample of the second material in the second conduit.

9. The device of claim 8 further characterized by:
a separator tank (222) having a top half and a bottom half, where the first conduit (208) flows into the separator tank (222) and the second conduit (210) is coupled to the bottom half of the separator tank.

10. The device of claim 8, further characterized by:
a second Coriolis flow meter (114) attached to the first conduit (108) and configured to measure the density of the liquid flowing in the first conduit;
a processor (120) connected to the first and second Coriolis flow meters and configured to determine the ratio of the first material with respect to the second material in the liquid in the conduit based, in part, on the density measurement from the first Coriolis flow meter.

11. The device of claim 8 characterized by the first conduit having a first diameter and the second conduit having a second diameter and the first diameter is larger than the second diameter.

12. The device of claim 11 characterized by the second diameter is less than 1/10 the first diameter.

13. The device of claim 8 characterized by the first conduit having a first flow rate and the second conduit having a second flow rate and the first flow rate is larger than the second flow rate.

* * * * *